(12) United States Patent
Tanaka et al.

(10) Patent No.: US 7,588,721 B2
(45) Date of Patent: Sep. 15, 2009

(54) METHOD FOR STORING XYLYLENEDIAMINE

(75) Inventors: Kazumi Tanaka, Niigata (JP); Kazuhiko Amakawa, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/846,873

(22) Filed: Aug. 29, 2007

(65) Prior Publication Data

US 2007/0297943 A1 Dec. 27, 2007

Related U.S. Application Data

(62) Division of application No. 10/981,660, filed on Nov. 5, 2004, now abandoned.

(30) Foreign Application Priority Data

Nov. 6, 2003 (JP) ............... 2003-377159

(51) Int. Cl.
*B01J 19/06* (2006.01)
(52) U.S. Cl. ............... 422/40; 62/66; 62/344; 564/372; 564/415
(58) Field of Classification Search ........... 564/415, 564/372; 422/40; 62/66, 344
See application file for complete search history.

(56) References Cited

U.S. PATENT DOCUMENTS 3,009,957 A * 11/1961 Adam ............ 564/385
5,693,862 A 12/1997 Keyvani et al.
6,646,163 B2 11/2003 Nakamura et al.

OTHER PUBLICATIONS

Chinese Official Action, for Application No. 200410082276.5, dated Nov. 3, 2006.
English abstract for EP 1 279 661, counterpart to CN 1397543, Published: Feb. 19, 2003.
European Search Report for Application No. EP 04 10 5246, dated Mar. 18, 2005.
Mitsubishi Gas Chemical Company, Inc., "Product name: PXDA", Material Safety Data Sheet, dated Jan. 2, 1998, pp. 1-6 (XP002310464).
Mitsubishi Gas Chemical Company, Inc., "Product name: PXDA", Material Safety Data Sheet, dated Nov. 11, 1998, pp. 1-7 (XP002310465).
Anonymous, "1,3-Bis(Aminomethyl)Benzene", International Chemical Safety Cards, dated Oct. 11, 2002 (XP-002310499).

* cited by examiner

*Primary Examiner*—Sean E Conley
(74) *Attorney, Agent, or Firm*—Antonelli, Terry, Stout & Kraus, LLP.

(57) ABSTRACT

A solid xylylenediamine solidified in a container is extremely excellent in storage stability as compared with a liquid xylylenediamine, and is less degraded by discoloration even when stored in an atmosphere containing oxygen. By charging a liquid xylylenediamine into a container, solidifying the liquid xylylenediamine into a solid xylylenediamine in the container under cooling without delay after the charging, and storing the solid xylylenediamine in the container while maintaining the xylylenediamine in a solid state, the xylylenediamine is stored for a long period of time without causing deterioration of quality such as discoloration.

8 Claims, No Drawings

METHOD FOR STORING XYLYLENEDIAMINE

This application is a Divisional application of application Ser. No. 10/981,660, filed Nov. 5, 2004 now abandoned, the contents of which are incorporated herein by reference in their entirety.

BACKGROUND OF THE INVENTION

1. Field of the Invention

The present invention relates to a solid xylylenediamine in a container, a production method thereof, and a method for storing xylylenediamine. The solid xylylenediamine in a container of the invention is quite stable on storing, and therefore, industrially useful. The xylylenediamine is a useful compound as a raw material for polyamide resins, curing agents, etc. and as an intermediate material for isocyanines compounds, etc.

2. Description of the Prior Art

Amines are liable to undergo the change of their quality by light, heat, oxygen, etc. and are well known to suffer from deterioration such as discoloration, change into odorous substance, etc. during their storage. Unlike aromatic amines such as diaminotoluene compounds and apliphatic amines such as hexamethylenediamine and isophoronediamine, the xylylenediamine structurally belongs to benzylamines. Therefore, the xylylenediamine is extremely susceptible to autoxidation and deammodation as compared with the aromatic amines and the aliphatic amines. Conventionally, the xylylenediamine has been stored in a sealed container having its inner air replaced by an inert gas such as nitrogen gas while being kept apart from the influence of light, heat, etc. In spite of such efforts, a satisfactory result is still not obtained.

As to the technique for stably storing the xylylenediamine, JP 46-21857 B discloses to add an unsaturated compound having a terminal double bond such as 1-butene, 1-hexene and styrene. However, the proposed method lowers the purity of final products because of inclusion of the additive. Alternatively, some disadvantages attributable to the added unsaturated compound may be caused during the use of final products.

JP 10-81651 A teaches that the generation of ammonia odor due to the degradation during storage can be prevented by storing a liquid aliphatic polyamine in a sealed container under a substantially oxygen-free condition. According to the examination made by the inventors, however, the xylylenediamine after storage was degraded and discolored even when the xylylenediamine was stored in drum cans and 20-L cans, which are industrially generally used as containers for storing the xylylenediamine, after replacing the inner atmosphere thereof by nitrogen in advance of charging the xylylenediamine into the containers under a flow of nitrogen. It seems that the "substantially oxygen-free condition" taught by JP 10-81651 A was not actually attained because oxygen could not be removed sufficiently by the nitrogen-replacement methods which have been employed in industrial productions to achieve the substantially oxygen-free condition. In fact, in the examination made by the inventors on the storage of xylylenediamine in 20-L cans, the oxygen content of the headspace in the 20-L cans was about 500 to 2000 ppm, although the 20-L cans had been purged with nitrogen in advance of changing the xylylenediamine under a flow of nitrogen. In addition, the oxygen content of the headspace in the 20-L cans after storage was higher than just after completing the charge of the xylylenediamine. This seems to be due to the penetration of air into the cans during storage. Therefore, to store the xylylenediamine under the substantially oxygen-free condition, special cares must be taken during the charge and in selecting the containers and packings so as to prevent the penetration of oxygen into the containers. However, the techniques usually employed in industrial process have been insufficient for achieving the substantially oxygen-free condition.

Not related to the storage of aromatic ring-containing aliphatic amine such as xylylenediamine, JP 2002-193897 A teaches that the quality of aromatic amines can be maintained without discoloration by storing under a sealed condition in the presence of an oxygen absorbing agent and a desiccant. Generally, the oxygen absorbing agent needs moisture to exhibit its function. Therefore, there will be a deterioration of quality due to the moisture entered into the amines. To prevent this problem, the desiccant is combinedly used. However, the use of desiccant makes it difficult to maintain the moisture content at a sufficient level for allowing the oxygen absorbing agent to exhibit its function. High-purity amines are extremely hygroscopic and have a moisture-absorbing speed comparable to common desiccants such as silica gel, activated carbon, molecular sieve and anhydrous calcium chloride. Therefore, it is practically impossible to completely absorb the moisture by the desiccant, namely, to completely prevent the moisture from entering into the amines.

In addition, since the pressure of headspace in the container is reduced by the absorption of oxygen, the proposed method has another problem such as deformation of container. To solve this problem, the use of a pressure container that is able to withstand the negative pressure is needed. The packing for the closure of container is also required to have gas-barrier properties to maintain a hermetic seal. Therefore, the containers usable in the proposed method are of a type not applicable to wide purposes.

SUMMARY OF THE INVENTION

An object of the invention is to provide a xylylenediamine which is excellent in storage stability and undergoes no deterioration of quality such as discoloration even in a long-term storage, a production method thereof and a method for storing xylylenediamine.

As a result of extensive research, the inventors have found that a solid xylylenediamine in a container which is produced by charging a liquid xylylenediamine into the container and then solidifying it in the container is quite excellent in storage stability, and therefore, can be stably stored for a long term without causing discoloration during the storage. The invention has been accomplished on the basis of this finding.

Thus, the invention provides a solid xylylenediamine in a container which is produced by solidifying a liquid xylylenediamine having an APHA color number of 20 or less in the container, the solid xylylenediamine having an APHA color number of 20 or less when measured after stored in a solid state and then melted into a liquid state. In a preferred embodiment, the oxygen content of the headspace (a space left between the charged xylylenediamine and the end of closure of the container) in the container is preferably regulated within 0.01 to 21% by volume. In another preferred embodiment, the xylylenediamine is preferably m-xylylenediamine or a mixture of m-xylylenediamine and p-xylylenediamine having a solidification point of 30° C. or lower.

The invention further provides a method for producing a solid xylylenediamine in a container, which comprises a step of charging a liquid xylylenediamine having an APHA color number of 20 or less into the container, and a step of solidifying the liquid xylylenediamine in the container by cooling.

In a preferred embodiment, the liquid xylylenediamine is solidified in the container after replacing the headspace in the container with an inert gas. In another embodiment, the liquid xylylenediamine is solidified within 10 days after charged into the container.

The invention still further provides a method for storing xylylenediamine, which comprises: charging a liquid xylylenediamine having an APHA color number of 20 or less into a container; solidifying the liquid xylylenediamine into a solid xylylenediamine in the container by cooling; and storing the solid xylylenediamine in the container while keeping the xylylenediamine in a solid state. In a preferred embodiment, the oxygen content of the headspace in the container is preferably regulated within 0.01 to 21% by volume.

Since the solid xylylenediamine in a container provided by the invention is quite excellent in storage stability, the deterioration due to discoloration hardly occurs even when stored in an atmosphere containing oxygen, for example, in air. The invention allows the use of inexpensive general-purpose containers which have been commonly used in industrial process, and does not require to exhaustively reduce the oxygen concentration of the storing atmosphere. Therefore, the invention provides an simple and economical storing method and has great industrial values.

DETAILED DESCRIPTION OF THE INVENTION

The invention will be described in more detail. The xylylenediamine referred to herein includes m-xylylenediamine, p-xylylenediamine and a mixture thereof. The solidification point of m-xylylenediamine is 14° C., and 63° C. for p-xylylenediamine. The solidification point of the mixture of m-xylylenediamine and p-xylylenediamine varies from 2 to 63° C. depending on the proportion thereof. Particularly preferred are m-xylylenediamine and a mixture of m-xylylenediamine and p-xylylenediamine having a solidification point of 30° C. or lower.

The solid xylylenediamine in a container is produced by charging a liquid xylylenediamine having an APHA color number of 20 or less into the container and then solidifying the liquid xylylenediamine in the container under cooling. If the APHA color number exceeds 20, the resultant solid xylylenediamine is significantly discolored to fail in achieving a sufficient quality. To maintain the APHA color number at 20 or less, it is preferred to control the storing history of the xylylenediamine after taken out of the production system until solidified in the container so as to satisfy the following conditions represented by the following formula:

$$0 < a \times b \times x \exp(0.07 \times T) < 2000$$

wherein a is an average oxygen concentration (% by volume) of the storing atmosphere, b is a period (days) taken after taking out of the production system until solidifying in the container, and T is an average temperature (° C.).

The liquid xylylenediamine charged into the container is desired to be solidified as soon as possible, preferably within 10 days, more preferably within 5 days, and particularly preferably within 3 days after charged into the container. The solidification temperature is not particularly limited. In view of solidifying as rapidly as possible, the solidification temperature is preferably 5° C. or more lower than the solidification point of the xylylenediamine. The liquid xylylenediamine is solidified under cooling, for example, by allowing the container to stand at a place of temperatures lower than the solidification point such as thermostatic room, refrigerator and outdoor in cold districts, by immersing the container in water bath, oil bath, etc, or by sprinkling powdery dry ice to the container.

The APHA color number of the solid xylylenediamine in a container after stored in a solid state is 20 or less when measured on a liquid xylylenediamine obtained by melting the stored solid xylylenediamine. The period of storing the solid xylylenediamine is preferably 5 to 1500 days, more preferably 30 to 800 days. If the APHA color number is 20 or less after storing for the period described above, the stored xylylenediamine is suitably used in various applications. The APHA color number is measured immediately after melting the solid xylylenediamine into the liquid xylylenediamine under heating so as to prevent the liquid xylylenediamine from being degraded by discoloration during the course between the melting step and the measurement, preferably melting the solid xylylenediamine after replacing the headspace of the container with an inert gas such as nitrogen. The methods of measuring the APHA color number are described in ASTM-D-1209 and ASTM-D-5386. In the actual measurement, either of a visual comparison with standard samples or a method using a commercially available colorimeter may be employed.

In the invention, various types of containers such as cans, bottles, containers and tanks each being made of metals, plastics or glass are usable. Unlike the liquid xylylenediamine, the solid xylylenediamine in a container exhibits an excellent storage stability even under a storing atmosphere containing oxygen. Therefore, a special container of highly airtight and a special packing of high gas-barrier properties are not needed to be used in the invention, and instead, cheap general-purpose containers, which have been commonly used in industrial process, such as drum cans, oil cans, tank lorries, bulk containers and stationary tanks are usable.

Surprisingly, the solid xylylenediamine in a container is extremely excellent in the storage stability as compared with the liquid xylylenediamine, and therefore, undergoes very little degradation due to discoloration even when stored under an atmosphere containing oxygen. This feature of the solid xylylenediamine is quite advantageous for handling the xylylenediamine. Since being susceptible to degradation by oxygen in air, the liquid xylylenediamine should be hermetically stored after replacing the air inside a container with an inert gas such as nitrogen. To achieve an oxygen-free condition, a long-term replacing operation using a large amount of inert gas is needed, and additionally, the container is required to be made into a special structure and made of a special material which is highly airtight enough to prevent the surrounding air from entering into the container during storage. However, the industrial process including these efforts cannot be simple and economical. On the contrary, the headspace of container is not necessarily required to be filled with inert gas such as nitrogen, instead, may be filled with air in the invention, because the solid xylylenediamine in a container is extremely resistant to degradation due to discoloration even under an atmosphere containing oxygen.

If the period from charging the liquid xylylenediamine into a container until solidifying it is long, or if the liquid xylylenediamine after melting the stored solid xylylenediamine is further stored in the container for a long time, namely, if the xylylenediamine is retained in the container in a liquid state for a long time, it is preferred in view of avoiding the degradation to replace the headspace in advance with a gas, such as nitrogen, argon and helium, which is free from oxygen and inert to the xylylenediamine. The oxygen concentration of the headspace is preferably 0.01 to 21% by volume, more preferably 0.01 to 1% by volume, and particularly preferably 0.01 to 0.3% by volume.

The invention further provides a novel method for storing the xylylenediamine utilizing the high storage stability of the solid xylylenediamine in a container. In the method, the xylylenediamine is stably stored by charging a liquid xylylenediamine having an APHA color number of 20 or less into a container, solidifying the liquid xylylenediamine into a solid xylylenediamine under cooling, and storing the solid xylylenediamine while maintaining it in a solid state.

The method of the invention is extremely advantageous, because the xylylenediamine is stably stored even when the headspace contains oxygen, particularly even when the headspace is air. For example, when the xylylenediamine in a container is left after the use at a place where inert gas is not available as in the case of using the xylylenediamine as a curing agent for epoxy resin at a building site, the degradation of the xylylenediamine left over can be effectively prevented by stably storing it by the method of the invention.

The oxygen concentration of the headspace during the storage of the solid xylylenediamine in a container while maintaining it in a solid state is preferably 0.01 to 21% by volume, more preferably 0.01 to 1% by volume, and particularly preferably 0.01 to 0.3% by volume. The lower the oxygen concentration is, the more expedient for preventing the degradation of the liquid xylylenediamine. In the storing method of the invention, however, a strict oxygen-free condition is not necessarily required and the presence of about 0.01% by volume of oxygen is acceptable, because the xylylenediamine presents in a liquid state only in a short period of time. According to the examinations made by the inventors, the oxygen concentration of the headspace can be easily reduced to 0.3 to 1% by volume by introducing an inert gas into the container. However, although not technically impossible, a long-term replacing operation using an excessively large amount of inert gas is required to achieve an extremely low oxygen concentration, particularly, of less than 0.01% by volume, because the efficiency of replacement by introducing inert gas lowers as the oxygen concentration is reduced. Since the presence of about 0.01% by volume of oxygen is allowable in the invention, the amount of the inert gas to be used and the operating time for replacement can be favorably reduced or shortened even in case of replacing the headspace of the container with an inert gas.

In the storing method of the invention, the storing temperature is regulated so as to allow the solid xylylenediamine to maintain its solidified condition. The storing temperature is not particularly limited so long as the solidified condition is maintained. In view of efficiency, the storing temperature is preferably within the range of −20° C. to a temperature that is 1° C. lower than the solidification point of the xylylenediamine. The temperature during storing the xylylenediamine in a solidified condition is not needed to be constant. If the atmospheric temperature is not higher than a temperature that is 1° C. lower than the solidification point of the xylylenediamine, a container charged with the xylylenediamine may be stored outdoors. However, cares should be taken so as to prevent the temperature of container from being raised over a temperature that is 1° C. lower than the solidification point of the xylylenediamine by direct exposure to sunlight, etc.

It is important for the production of the solid xylylenediamine in a container to solidify the liquid xylylenediamine after charging it into the container. It is not preferred to charge the flakes obtained by crushing the solidified xylylenediamine into the container, particularly when the headspace is replaced with an inert gas such as nitrogen in advance of the storage, because the replacement requires a long period of time or the replacement is not effected sufficiently because of a large amount of gas included in the xylylenediamine flakes.

The xylylenediamine is used usually in a liquid condition in applications such as curing agents for epoxy resins, raw materials for polyamide and raw materials for isocyanates. The solid xylylenediamine is preferably melted in the container for the subsequent use by various melting methods, for example, by leaving the container at a place of a temperature higher than the solidification point, by immersing the container in a water bath, an oil bath, etc., by bringing a band heater, etc. into contact with the container, or by spraying steam onto the container. The temperature for melting is preferably as low as possible. Therefore, the solid xylylenediamine is melted at temperatures preferably lower than "solidification point+120° C.," more preferably lower than "solidification point+60° C.," and still more preferably lower than "solidification point+40° C." It is preferred to replace the headspace with an inert gas such as nitrogen before melting when the headspace is air or contains oxygen.

Metals such as cobalt, copper, rhodium, zinc and iron adversely affect the storage stability of the xylylenediamine. Therefore, the total content of cobalt, copper, rhodium, zinc and iron in the xylylenediamine is preferably reduced to 0.005% by weight or less, more preferably 0.0005% by weight or less.

The invention will be described in detail with reference to examples and comparative examples. However, it should be noted that the scope of the invention is not limited to the examples.

The discoloration was evaluated by the APHA color number measured according to the method of ASTM-D-1209.

EXAMPLE 1

Into a 0.5-L brown glass bottle, 0.4 L of 25° C. liquid m-xylylenediamine (APHA color number ≦5, 14° C. solidification point) was charged in air. Immediately after sealing, the bottle was stored in a thermostatic chamber at 2° C. After 2 h of storage in the thermostatic chamber, the solidification of m-xylylenediamine was visually confirmed. After one month (30 days) of storage at 2° C., the glass bottle containing m-xylylenediamine was taken out of the thermostatic chamber and immersed in a water bath of 40° C. to melt the stored solid m-xylylenediamine for the measurement of APHA color number. The measured APHA color number was 5 or less, indicating that no discoloration occurred during the storage.

EXAMPLE 2

Into a 0.5-L brown glass bottle, 0.4 L of 25° C. liquid meta/para xylylenediamine mixture (meta/para=7/3 by mol, APHA color number ≦5, 8° C. solidification point) was charged in air. Immediately after sealing, the bottle was stored in a thermostatic chamber at 2° C. After 2 h of storage in the thermostatic chamber, the solidification of xylylenediamine was visually confirmed. After one month (30 days) of storage at 2° C., the glass bottle containing xylylenediamine was taken out of the thermostatic chamber and immersed in a water bath of 40° C. to melt the stored solid xylylenediamine mixture for the measurement of APHA color number. The measured APHA color number was 5 or less, indicating that no discoloration occurred during the storage.

EXAMPLE 3

Into a 20-L metal container, 18 L of 25° C. liquid m-xylylenediamine (APHA color number ≦5, 14° C. solidification point) was charged. Immediately after replacing the headspace with nitrogen by blowing nitrogen for one minute, the container was sealed. The container was left standing at 5 to 13° C. to store m-xylylenediamine in a solid state for two months (60 days). After two months of storage, the stored solid m-xylylenediamine was melted in a water bath of 40° C. for the measurement of APHA color number. The measured APHA color number was 5 or less, indicating that no discoloration occurred during the storage. The oxygen content of the headspace after the storage was 0.15% by volume.

EXAMPLE 4

Into a 0.5-L brown glass bottle, 0.4 L of 80° C. liquid p-xylylenediamine (APHA color number ≦5, 63° C. solidification point) was charged in air. Immediately after replacing the headspace with nitrogen by blowing nitrogen for one minute, the bottle was sealed and stored in a thermostatic chamber at 2° C. After 2 h of storage in the thermostatic chamber, the solidification of p-xylylenediamine was visually confirmed. After one month (30 days) of storage at 2° C., the glass bottle containing p-xylylenediamine was taken out of the thermostatic chamber and immersed in a water bath of 80° C. to melt the stored solid p-xylylenediamine for the measurement of APHA color number. The measured APHA color number was 5 or less, indicating that no discoloration occurred during the storage.

COMPARATIVE EXAMPLE 1

Into a 0.5-L brown glass bottle, 0.4 L of 25° C. liquid m-xylylenediamine (APHA color number ≦5, 14° C. solidification point) was charged in air. After sealing, the bottle was left standing at room temperature (25° C.) to store m-xylylenediamine in a liquid state for one month (30 days), and then, APHA color number was measured. The measured APHA color number was 60, showing a significant discoloration into yellow.

COMPARATIVE EXAMPLE 2

Into a 0.5-L brown glass bottle, 0.4 L of 25° C. liquid meta/para xylylenediamine mixture (meta/para=7/3 by mol, APHA color number ≦5, 8° C. solidification point) was charged in air. After sealing, the bottle was left standing at room temperature (25° C.) to store the mixture in a liquid state for one month (30 days), and then, APHA color number was measured. The measured APHA color number was 50, showing a significant discoloration into yellow.

COMPARATIVE EXAMPLE 3

Into a 20-L metal container, 18 L of 25° C. liquid m-xylylenediamine (APHA color ≦5, 14° C. solidification point) was charged. Immediately after replacing the headspace with nitrogen by blowing nitrogen for one minute, the container was sealed. The container was left standing at 20 to 30° C. to store m-xylylenediamine in a liquid state for two months (60 days). After two months of storage, APHA color number was measured. The measured APHA color number was 25, showing an apparent discoloration.

The xylylenediamine to be stored in the method of the invention is useful as a raw material for polyamide resins, curing agents, etc. and as an intermediate material for isocyanate compounds, etc.

What is claimed is:

1. A method for storing xylylenediamine, which comprises:
   charging a liquid xylylenediamine having an APHA color number of 20 or less into a container;
   solidifying the liquid xylylenediamine into a solid xylylenediamine in the container by cooling; and
   storing the solid xylylenediamine in the container while keeping the xylylenediamine in a solid state, wherein the solid xylylenediamine is stored at a temperature within a range of −20° C. to a temperature that is 1° C. lower than the solidification point of the xylylenediamine.

2. The method according to claim 1, wherein an oxygen concentration in a headspace in the container is 0.01 to 21% by volume.

3. The method according to claim 1, wherein the xylylenediamine is m-xylylenediamine or a mixture of m-xylylenediamine and p-xylylenediamine having a solidification point of 30° C. or lower.

4. The method according to claim 1, wherein the liquid xylylenediamine is solidified within 10 days after being charged into the container.

5. The method according to claim 1, wherein the liquid xylylenediamine is solidified at a solidification temperature 5° C. or more lower than the solidification point of the xylylenediamine.

6. The method according to claim 1, wherein the solid xylylenediamine is stored for 5 to 1500 days.

7. The method according to claim 1, wherein after the solidifying, the container containing the solid xylylenediamine is left as it is for the storing.

8. A method for storing xylylenediamine, which comprises:
   charging a liquid xylylenediamine having an APHA color number of 20 or less into a container;
   solidifying the liquid xylylenediamine into a solid xylylenediamine in the container by cooling; and
   storing the solid xylylenediamine in the container while keeping the xylylenediamine in a solid state, wherein the solid xylylenediamine is stored for 5 to 1500 days.

* * * * *